US006322570B1

(12) United States Patent
Matsutani et al.

(10) Patent No.: US 6,322,570 B1
(45) Date of Patent: Nov. 27, 2001

(54) NEEDLE HOLDER FOR GUIDING NEEDLE WITH SUTURE

(75) Inventors: Kanji Matsutani; Masatoshi Fukuda, both of Tochigi-ken (JP)

(73) Assignee: Mani, Inc., Tochigi-ken (JP)

( * ) Notice: Subject to any disclaimer, the term of this patent is extended or adjusted under 35 U.S.C. 154(b) by 0 days.

(21) Appl. No.: 09/365,234

(22) Filed: Jul. 30, 1999

(51) Int. Cl.$^7$ .................................................... A61B 17/04

(52) U.S. Cl. .......................... 606/145; 606/139; 606/148

(58) Field of Search .................................... 606/144–148, 606/139; 128/340

(56) References Cited

U.S. PATENT DOCUMENTS

| | | | | |
|---|---|---|---|---|
| 3,349,772 | * | 10/1967 | Rygg | 606/145 |
| 3,470,875 | * | 10/1969 | Johnson | 606/145 |
| 4,161,951 | * | 7/1979 | Scanlan, Jr. | 128/340 |
| 4,957,498 | * | 9/1990 | Caspari et al. | 606/146 |
| 5,824,009 | * | 10/1998 | Fukuda et al. | 606/144 |
| 5,993,466 | * | 11/1999 | Yoon | 606/147 |
| 6,004,332 | * | 12/1999 | Yoon et al. | 606/144 |

* cited by examiner

*Primary Examiner*—David O. Reip
*Assistant Examiner*—Julian W Woo
(74) *Attorney, Agent, or Firm*—Townsend & Banta

(57) ABSTRACT

A needle holder for guiding a surgical needle having a suture attached to the needle, in which the surgical needle is transferred from a first shaft to a second shaft, comprising a needle stand formed on the first shaft and a needle receiver formed on the second shaft, receiving the needle made upright at the needle stand. Further, the needle holder comprises a guide passage formed on the first shaft for guiding the suture attached to the needle from the needle stand in a prescribed direction to at least the vicinity of the needle stand, the guide passage having a surface that has no edge damaging the suture in a cross direction with respect to the direction of the tension exerted to the suture.

4 Claims, 10 Drawing Sheets

| | | | | | | | | | |
|---|---|---|---|---|---|---|---|---|---|
| 1 | Needle diameter(mm) | 1.5 | 1.4 | 1.3 | 1.2 | 1.1 | 1.0 | 0.9 | 0.8 |
| 2 | Maximum exe size(mm) | 1.2 | 1.12 | 1.04 | 0.96 | 0.88 | 0.80 | 0.72 | 0.64 |
| 3 | Maximum suture(USP) | 10 | 9 | 8 | 7 | 6 | 5 | 5 | 3~4 |
| 4 | Suture attaching force of normal product (kgf) | 2.1 | 2.1 | 2.1 | 2.1 | 2.1 | 2.1 | 2.1 | 2.1 |
| 5 | Needle retaining force (kgf) | 1.5 | 1.4 | 1.3 | 1.2 | 1.1 | 1.0 | 0.9 | 0.8 |
| 6 | Needle diameter | 2.25 | 2.1 | 1.95 | 1.8 | 1.65 | 1.5 | 1.35 | 1.2 |

| | | | | | | | | | | |
|---|---|---|---|---|---|---|---|---|---|---|
| 1 | 0.6 | 0.5 | 0.4 | 0.3 | 0.2 | 0.1 | 0.07 | 0.05 | 0.03 | 0.01 |
| 2 | 0.48 | 0.40 | 0.32 | 0.24 | 0.16 | 0.08 | 0.056 | 0.04 | 0.024 | 0.008 |
| 3 | 1 | 0 | 2−0 | 3−0 | 4−0 | 6−0 | 7−0 | 8−0 | 10−0 | 11−0 |
| 4 | 1.8 | 1.35 | 1.35 | 1.02 | 0.69 | 0.24 | 0.12 | 0.075 | 0.030 | 0.015 |
| 5 | 0.6 | 0.5 | 0.4 | 0.3 | 0.2 | 0.1 | 0.07 | 0.05 | 0.03 | 0.01 |
| 6 | 0.9 | 0.75 | 0.6 | 0.45 | 0.3 | 0.15 | 0.105 | 0.075 | 0.045 | 0.015 |

FIG. 12

NEEDLE HOLDER FOR GUIDING NEEDLE WITH SUTURE

BACKGROUND OF THE INVENTION

1. Field of the Invention

This invention relates to a needle holder for guiding a needle with a suture attached to the needle (hereinafter, simply referred to as "a needle holder") for ligating blood vessels or suturing tissues by penetrating such as a surgical needle engaging a suture among living tissues of patients or by passing the surgical needle through tissues and, more particularly, to a needle holder for guiding a needle providing sure connection of the suture in avoiding disconnection of the suture in a midway or disengagement of the suture at an engagement portion where the suture is tensioned.

2. Description of Related Art

Endoscopic surgery is widely executed these days in which the patient receives lighter burden by incising a minimum abdominal area, passing an instrument through the small incised area, and operating the tool in use of an endoscope and the like. Needle holders, to do such operations, as well as to ligate vessels or suture tissues in a deep, narrow area even in general operations such as opening an abdominal portion or chest portion, have been devised in which a surgical needle with a suture held at a needle stand formed on one shaft of the needle holder is transferred to a needle receiver formed on the other shaft of the needle holder, and such needle holders are utilized for ligating and suturing affected portions to be operated. Such a needle holder allows operations to be executed in an area generally tough for surgeons or other professionals, namely, in an area subjecting to an endoscopic surgery or in a deep portion or narrow portion in a body.

As a needle holder for a needle with a suture attached thereto for operations, there is as described in e.g., Japanese Unexamined Patent Publication (KOKAI) No. 9-56,719. Such a needle holder has a simple structure that a pair of shafts moves as to be open and closed, thereby transferring the needle with the suture from the needle stand to the needle receiver easily and surely.

Such a conventional needle with a suture is always subject to a certain tension because the user of the needle holder does operation in giving tension to one end of the suture. In such a case, where a portion far from the suture is pulled in a longitudinal direction of the holder, the needle is made upright in a crossing direction to the direction of the tension exerted to the far portion. The suture is therefore folded about 90 degrees around the needle stand, so that the suture may be damaged when in contact with an edge of the needle stand.

If the suture, particularly, a fine suture, is damaged, such a suture may be broken down when excessive force is given to the suture during the operation. If the edge increases frictional resistance between the edge and the suture, larger tension should apply to the suture and may increase the risk of disconnection of the suture. If the needle is separated from the suture within the body, the needle dropped in the body must be found and collected, which burdens unnecessarily on the surgeons and patients and therefore, it is a matter that should be avoided.

If the needle receiver keeps a needle with excessive retaining force, excessive tension may be exerted to the suture when the needle is taken out from the needle receiver by pulling the suture, thereby raising problems such that the suture may be disengaged from the needle or the suture may be cut off. In addition, such a retaining force cannot be determined in a quantitative manner notwithstanding the needle diameter because the range of force used by the operator may vary depending on the size and kind of organs of the patient to be operated, as well as the diameter and size of the needle.

It is an object of the invention to provide a needle holder for guiding a needle having a suture attached to the needle, capable of avoiding the suture from sustaining damages when operated and providing suitable feelings for use according to the characteristics of the respective operations by setting the needle retaining force of the needle receiver at a proper amount according to the needle diameter.

SUMMARY OF THE INVENTION

To solve the above problem, a needle holder for guiding a surgical needle having a suture attached to the needle according to the invention is a needle holder in which the surgical needle held on a needle stand on a first shaft is transferred to a needle receiver on a second shaft and in which the first shaft at least has a guide passage formed on the first shaft for guiding the suture attached to the needle from the needle stand in a prescribed direction to at least the vicinity of the needle stand without any edge damaging the suture in a cross direction with respect to the direction of the tension exerted to the suture.

With such a needle holder according to the invention, the direction of the tension exerted to the suture of the needle is changed by using the guide passage formed around the needle stand having no edge, thereby avoiding the suture from receiving damages during operation and ensuring operation with a higher certainty.

In another structure according to the invention, a needle holder for guiding a surgical needle having a suture attached to the needle according to the invention is a needle holder in which the surgical needle held on a needle stand on a first shaft is transferred to a needle receiver on a second shaft and in which the needle receiver allows the needle with the suture to be pulled out by pulling the suture when necessary and in which needle retaining force of the needle receiver on the second shaft is 0.005 kgf or greater but 2.1 kgf or less as well as 1.5 kgf multiplied by the diameter of the needle (mm) or less.

By rendering the needle retaining force at the needle receiver proportioned to the diameter of the needle and set to a proper amount, the needle holder becomes a needle holder with excellent feelings for use which can provide suitable feelings for use according to the characteristics of respective operations.

BRIEF DESCRIPTION OF THE DRAWINGS

The above and other objects and features of the invention are apparent to those skilled in the art from the following preferred embodiments thereof when considered in conjunction with the accompanied drawings, in which:

FIG. 12 is a table showing a desirable needle retaining force of a needle retainer at a needle receiver according to the invention.

DESCRIPTION OF PREFERRED EMBODIMENTS

Figure 1:
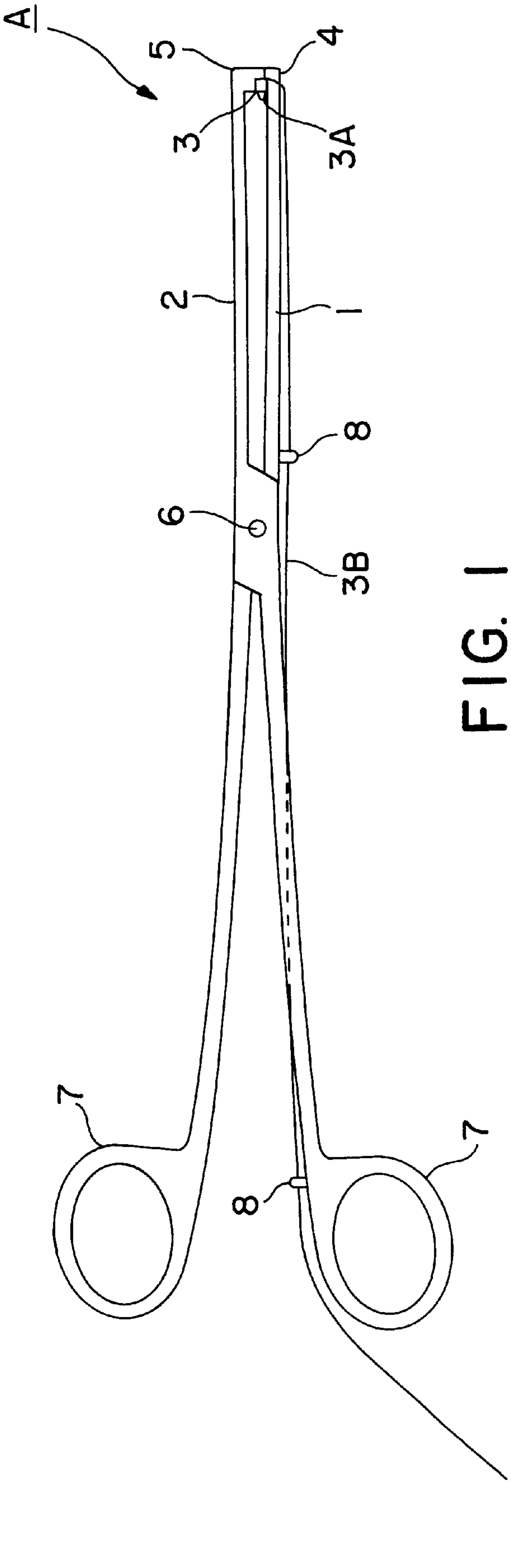
FIG. 1 is a side view showing a needle holder according to a first embodiment of the invention.
Figure 2:
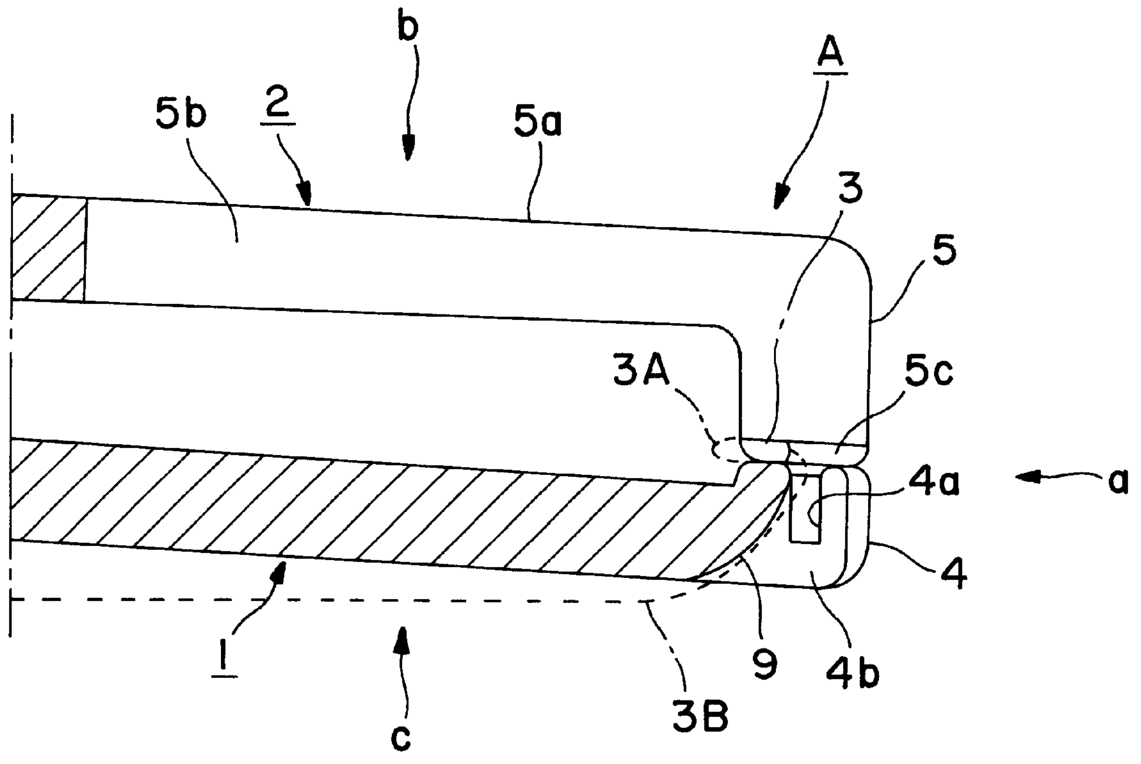
FIG. 2 is an enlarged side view showing a needle stand and a needle receiver of the needle holder.
Figures 3A, 3B, 3C:
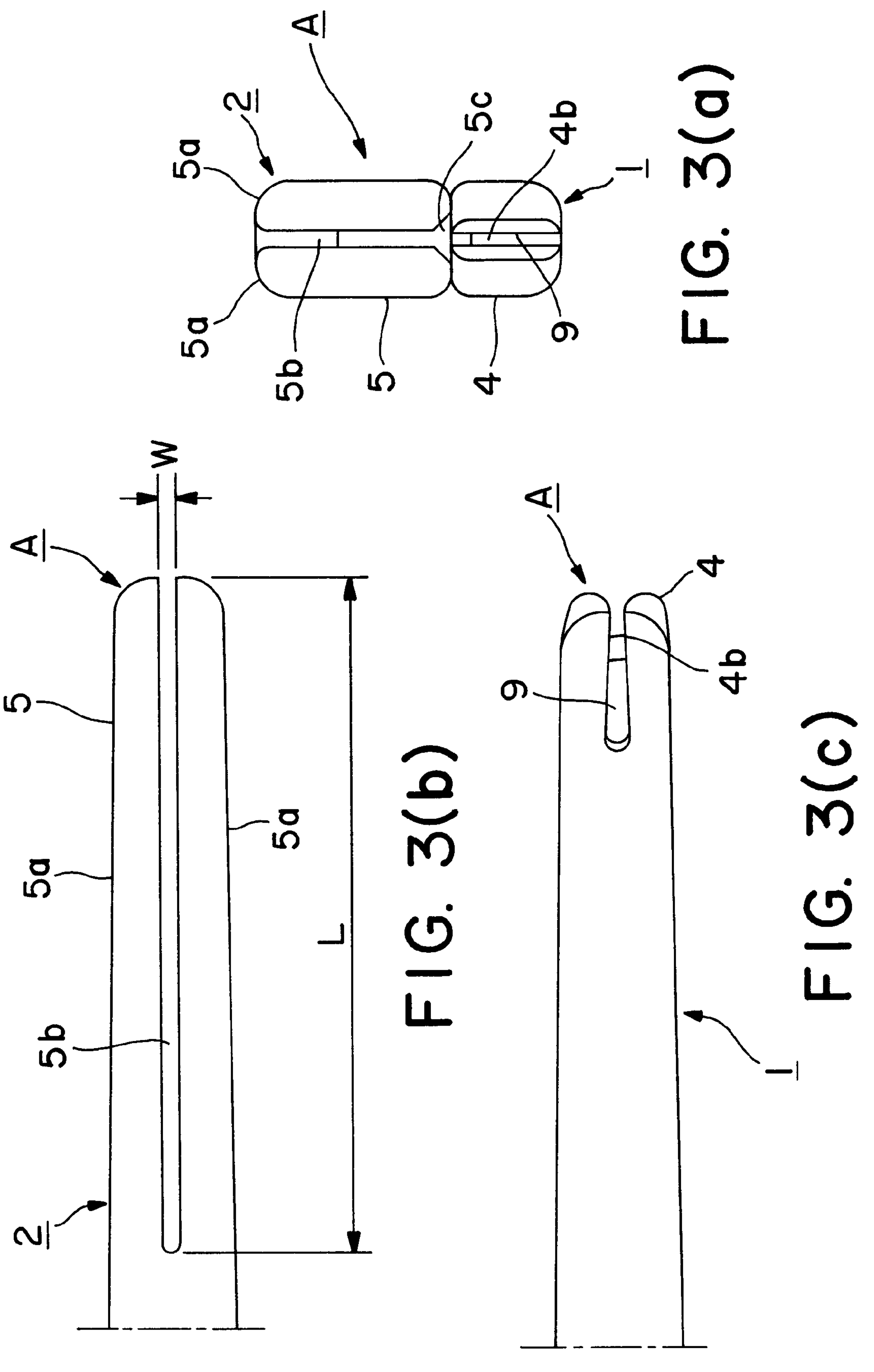
FIGS. 3(*a*) to 3(*c*) are views showing a distal end of the needle holder, in which FIG. 3(*a*) is a front view showing the distal end of the needle holder when seen in a direction of arrow a in FIG. 2, in which FIG. 3(*b*) is a plan view showing the distal end of the needle holder when seen in a direction of arrow b in FIG. 2, and in which FIG. 3(*c*) is a bottom view showing the distal end of the needle holder when seen in a direction of arrow c in FIG. 2.
Figure 4A:
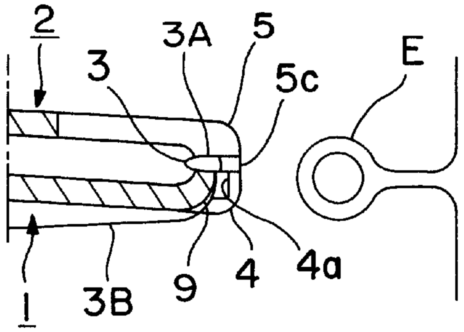
FIGS. 4(*a*) to 4(*d*) are illustrations showing how to use the needle holder.
Figure 4B:
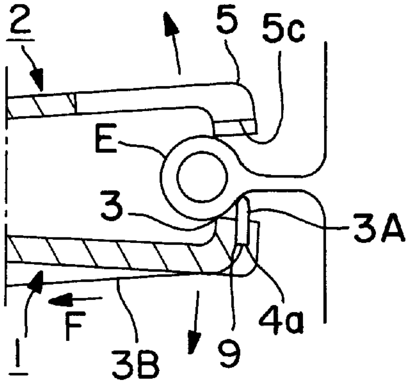
Figure 4C:
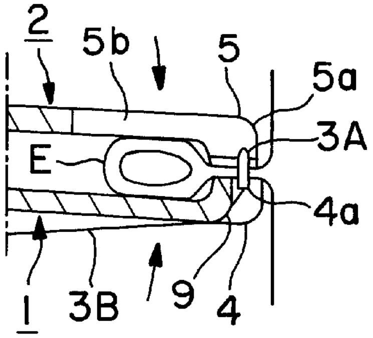
Figure 4D:
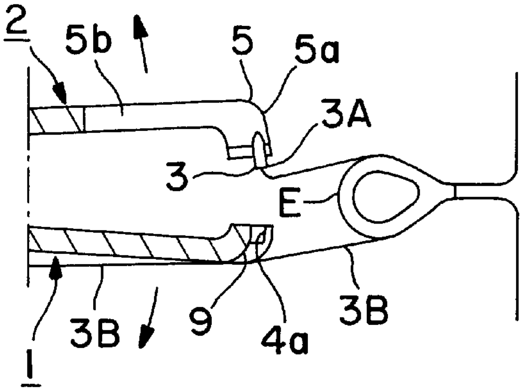

Referring to the drawings, preferred embodiments according to the invention are described in detail. FIG. 1 is a side view showing the whole portion of the needle holder according to this embodiment; FIG. 2 is an enlarged side view showing a needle stand and a needle receiver of the needle holder; FIGS. 3(*a*) to 3(*c*) are views showing the needle stand and the needle receiver when seen in directions of arrows a,b,c, respectively, in FIG. 2.

The needle holder A shown in FIG. 1 has levers 1, 2 made of a stainless steel forming a pair of shafts structured so as to be separate from and come closer to each other. One lever (first lever) 1 is formed with a needle stand 4 for rendering the needle with a suture upright, while the other lever (second lever) 2 is formed with a needle receiver 5 for receiving the needle 3 with the suture. The levers 1, 2 are pivotally connected around a pivotal pin 6 at a center of each in crossing over each other, and handles 7 are formed on respective of the other end of the receiver 5 and the stand 4, so that the needle holder A as a whole has substantially the same shape as a forceps.

The needle 3 having the suture is placed on the needle stand 4 formed on a distal end of the first lever 1. The needle 3 having the suture includes a needle body 3A, and a suture 3B attached to a proximal end of the needle body 3A. Engagement of the needle body 3A and the suture 3B is made by drilling an eye in the proximal end of the needle body 3A, inserting the end of the suture 3B in the eye and caulking the eye.

Plural suture guide members 8 are attached at prescribed positions to guide the suture 3B for the needle 3 from the needle stand 4 to the handle 7 along the lever 1. The user of the needle holder A pulls a proximal end of the suture 3B with a light force, and uses the needle holder A in applying tension to the suture 3B.

Using FIGS. 2, 3, the structures of the needle stand 4 and the needle receiver 5 are described. FIG. 2 is a side cross-sectional view of a distal end of the needle holder A, namely, portions of the needle stand 4 and the needle receiver 5, and FIGS. 3(*a*) to 3(*b*) are a plan view, a front view, and a bottom view, respectively, of the distal end of the needle holder A when seen in directions of arrows a,b,c, respectively, in FIG. 2.

The needle stand 4 formed on the distal end of the first lever 1 has a slit 4*b* to make the tip two-branched and is formed with a needle standing recess 4*a* opening upward so as to extend over the opposite sides. The needle stand recess 4*a* is a recess slightly larger than the needle body 3A of the needle 3 having the suture. As shown in FIG. 2, where the second lever is pulled up from the first lever while the suture 3B attached to a proximal end of the needle body 3A laid laterally between the first and second levers 1, 2 is pulled slightly, the needle body 3A can be fitted into the needle stand recess 4*a*. As shown in FIG. 2, the opening of the needle stand recess is chamfered so as not to form any edge to prevent the suture 3B from receiving damages when contacting to the opening while tension is given to the suture 3B.

A guide passage 9 for the suture 3B is formed along the slit 4*b* of the needle stand 4. The guide passage 9 has an inclined surface from a top end to a bottom end of the slit 4*b*, and when the needle 4 having the suture is placed at the needle stand 4, the guide passage 9 guides the suture 3B along the passage 9 as well as along the longitudinal direction of the first lever 1.

The needle receiver 5 is formed at the distal end of the second lever 2. The needle receiver 5 has a prescribed length L and a slit 5*b* having a width W smaller than the diameter of the needle body 3A and has clamping arms 5*a*, 5*a* on the opposite sides of the receiver. A needle retaining portion 5*c*, a space formed by the clamping arms 5*a*, 5*a* inclined in a reversed V shape astride the slit 5*b*, is formed at a portion where the needle receiver 5 contacts with the needle stand 4. The needle retaining portion 5*c* can hold the needle in a condition that the needle 3 having the suture is laid upon contacting the needle stand 4 with the needle receiver 5, and the needle retaining portion 5*c* also serves as a guide for leading the needle tip into the slit 5*b* where the needle 3 having the suture is made upright and transferred from the needle stand 4 to the needle receiver 5.

As shown in FIG. 3(*a*) as a front view of the needle stand 4 and the needle receiver 5, the needle retaining portion 5*c* has an opening on a front side. When the needle 3 having the suture is made ready for suturing, first, the needle stand 4 and the needle receiver 5 are separated as to render the needle holder A in an open state, and then, the needle body 3A of the needle 3 having the suture is placed as to be laid on the needle stand 4 from the front side. Subsequently, the needle stand 4 is made closer to the needle receiver 5, and the needle body 3A is held as the needle retaining portion 5*c* comes over the needle 3 having the suture. The suture 3B in engagement with the proximal end of the needle body 3A extends along the guide passage 9 through the slit 4*b* from the outside. This preparation is completed by passing the suture 3B though the suture guide members 8 on the first lever 1.

In the needle receiver 5, since the needle body 3A having the larger diameter than the width W of the slit 5*b* enters in the slit 5*b* when the needle receiver 5 contacts with the needle body 3A while the needle body 3A is made upright on the needle stand 4, the needle body 3A is surely held by the two clamping arms 5*a*, 5*a* from the opposite sides with frictional engagement upon widening the clamping arms 5*a*, 5*a* formed on opposite sides.

The force retaining the needle 3 having the suture at the needle receiver 5, though may vary depending on the surface states of the lever 2 and the needle body 3A, can be set to a proper retaining force as described below by changing mainly the length L (more precisely, a distance between the proximal end of the clamping arm 5*a* and the contacting portion of the needle body 3A) and the width W of the slit 5*b* formed at the needle receiver 5 where the diameter of the needle body 3A is presumed as constant. It was turned out that such a needle retaining force of the needle receiver 5 desirably takes amounts shown in Table in FIG. 12 as a result of a use test.

In a case that the needle holder A thus structured is used for suturing operation, sometimes, the needle body 3A once transferred from the needle stand 4 to the needle receiver 5 is returned again to the needle stand 4 to repeat the same work. In such a situation, the suture 3B is pulled to extract the needle body 3A from the needle receiver 5.

Particularly, in a case of delicate operation in which a fine needle having a small diameter is used (for example, a case such that a small blood vessel is ligated), the operation executor, or surgeon, desirably works with smaller force. To the contrary, in a case of operation requiring larger force using a needle having a larger diameter (for example, in a case that hard tissues are sutured), force of the surgeon becomes large.

In summary, the needle retaining force is proportioned to the feeling given to the surgeon when the needle enters (when the needle enters in the needle receiver 5). It is very difficult to confirm whether the needle 3A is surely entered in the needle receiver 5 through a monitor, and this feeling provides very important information to the surgeon. The feeling should be large when a large needle is used.

In consideration of the above matters, it is natural that the above work extracting the needle body 3A from the needle receiver 5 in pulling the suture 3B is done with force proportioned to the diameter of the needle body 3A, and optimum needle retaining force of the needle receiver 5, based on those facts, was obtained with respect to the respective diameters of the needles from the experimental results as shown in Table in FIG. 12.

From Table in FIG. 12, it is turned out that the needle retaining force owned by the needle receiver 5 is proportioned to the diameter of the needle body 3A and desirably set to about 1 kgf multiplied by the diameter (mm) of the needle body. The needle retaining forces shown in Table are measured values under a dried condition. If the needle holder A is actually used for operation, body fluid such as blood or the like works as a lubricant, and the actual needle retaining force is reduced more or less in comparison with the values shown in Table. Therefore, in consideration with a prescribed permissive range, it is desirable to set that the force is of 1.5 kgf multiplied by the diameter (mm) of the needle body.

On the other hand, according to Table shown in FIG. 12, when the needle diameter is 1.5 mm, the force may exceed 2.1 kgf. The needle holder A may hurt some healthy living tissues when the needle holder A is moved largely even for use of operation that a surgeon executes in viewing an endoscope (endoscopic operation). Therefore, it is not desirable to create a situation that the needle holder A has to be controlled by greater force even where the needle diameter is made thicker than the above diameter, so that it is preferable to set the upper limitation of the needle retaining force of the needle receiver 5 to 2.1 kgf. Where the force is set equal to or less than the suture attaching force of a commercially available needle having a suture, the needle holder also prevents the suture from disconnecting from the needle.

The lower limitation of the needle retaining force of the needle receiver 5 is set to 0.005 kgf to avoid a situation that the needle body 3A is disengaged from the needle receiver 5 due to a bit of contact.

From total consideration of the above matters, the needle holder A according to the invention has a needle retaining force of 0.005 kgf or greater but 2.1 kgf or less as well as 1.5 kgf multiplied by the diameter of the needle (mm) or less.

The needle retaining force of the needle receiver 5 is preferably set so that the needle body 3A is disengaged from the needle receiver 5 when the suture 3B is tensioned before the suture 3B is disengaged from the needle body 3A. Engagement force between the needle body 3A and the suture 3B (referred to as "suture attaching force") is obligated to have a minimum value according to the needle size from, e.g., USP standard or the like, but since normal products have suture attaching force three times of force defined in such a standard (see, section of "suture attaching force" in Table), any of the needle retaining force determined based on the above rule has a smaller value than the suture attaching force, so that the suture 3B will never be disengaged from the needle body 3A when the suture 3B is pulled.

Although in Table shown in FIG. 12 various conditions are indicated where the diameter of the needle body 3A is set at 0.01 mm to 1.5 mm, a desirable needle body 3A has the diameter of 0.1 mm or more and 1.0 mm or less because of handling easiness in terms of productivity of work.

The relation between the diameter of the needle body 3A and the diameter of the suture 3B can be, as a reference, such that a suture 3B having a diameter of 45% to 80% of the diameter of the needle body 3A may be used. As an structural example for the needle 3 having the suture, the needle body 3A is made of an austenite based stainless steel where the suture 3B is made of one of various materials such as silk, Nylon, polypropylene, absorption type (PGA) or the like.

FIG. 4 is an illustration showing a using method of the needle holder A. The needle holder A is used upon inserting the distal ends of the levers 1, 2 in an abdominal cavity from an incised section on the abdomen during operation, and the surgeon executes operation in watching images on a monitor and using an endoscope or the like. The needle holder A is used for works such as ligating blood vessels or suturing incised tissues, and herein, the ligating work for blood vessels is illustrated as an example.

First, as shown in FIG. 4(*a*), the levers 1, 2 are made closed, and the needle 3 having the suture is placed in a state that the needle 3 is laid between the needle stand 4 and the needle receiver 5. In keeping this state, the tip of the needle holder A is moved to be closer to a blood vessel E to be ligated.

When the tip of the needle holder A comes closer to the blood vessel E, the suture 3B is lightly pulled with small force F as shown in FIG. 4(*b*) to give tension to the suture 3B. Where the levers 1, 2 are separated, the proximal end of the needle body 3A is fitted into the needle stand recess 4*a* of the needle stand 4, thereby rendering the needle body 3A stand upright.

As shown in FIG. 4(*b*), then, the needle stand 4 and the needle receiver 5 come on opposite sides of the blood vessel E, and subsequently, as shown in FIG. 4(*c*), the levers 1, 2 are made closer to each other. This movement makes the needle body 3A standing upright on the needle stand 4 pass through living tissues located behind the blood vessel E and inserted in the slit 5*b* of the needle receiver 5 with pressure, thereby transferring the needle body 3A from the needle stand 4 to the needle receiver 5.

As shown in FIG. 4(*d*), the levers 1, 2 are made separated again from each other, and where separated from the blood vessel E, the needle holder A can wind the suture 3B around the blood vessel E. Subsequently, ligation of the blood vessel E is completed by forming a knot of the suture 3B (as a method for knotting the suture 3B describing in detail, see e.g., known methods as described in Japanese Unexamined Patent Publication (KOKAI) Heisei No. 9-299,375).

Figure 5:
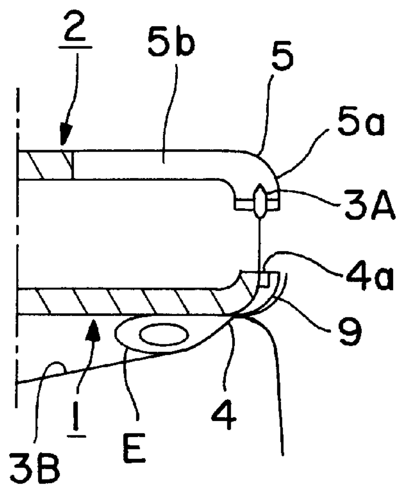
FIG. 5 is an illustration showing a continuous suturing operation using the needle holder.

FIG. 5 is an illustration showing an example of work done after the work shown in FIG. 4(*d*). Particularly, when suturing is made successively in the body, the suture 3B is pulled to return the needle body 3A again to the needle stand 4 after the needle body 3A is transferred once to the needle receiver 5 as shown in FIG. 5. In such a case, because the living tissues may be clamped between the instrument and the suture, the living tissues may be damaged due to friction from the suture if the needle retaining force is large. In a case of the holder according to the invention, the needle retaining force is limited within a certain range, and therefore, the needle body 3A is disengaged from the needle receiver before exertion of excessive force and moves to the needle stand, so that the living tissues would not be injured.

To do this work in fact, the levers 1, 2 are made closer to each other after entering in a state shown in FIG. 5, to receive the proximal end of the needle body 3A at the needle stand recess 4a of the needle stand 4, and subsequently, the levers 1, 2 are separated again in tensioning the suture 3B with force equal to or greater than the needle retaining force of the needle receiver, thereby moving the needle body 3A to the needle stand portion.

In the series of the works thus described, since the suture 3B always passes through the interior of the guide passage 9 inclined toward the needle stand 4 in the lever 1, the suture 3B is free from sustaining damages, so that the needle holder A can prevent the suture from accidentally cut off or accidentally disengaged. Particularly, when the tension is given to the suture 3B, the guide passage 9 smoothly changes the direction of the tension from the longitudinal direction of the lever 1 to the direction crossing to the longitudinal direction, thereby preventing a part of the suture 3B from subjecting to overburdened.

As described above, since the needle retaining force of the needle receiver 5 is determined by the diameter of the needle body 3A multiplied by a fixed rate and is set within a certain range having the upper limitation and the lower limitation, the needle holder A according to the embodiment has an excellent controllability during the series of works for operation, prevents mistakes in control from occurring, and makes a guide instrument without suture cutting off or disengagement.

Although in the needle holder A of the above embodiment has the guide passage 9 around the needle stand 4 only, another guide passage having a long groove extending the outer side of the lever 1 in excluding the suture guide members 8 may be formed as a matter of course, and similarly, another member may be formed to add a tension to the suture 3B.

Figure 6A:
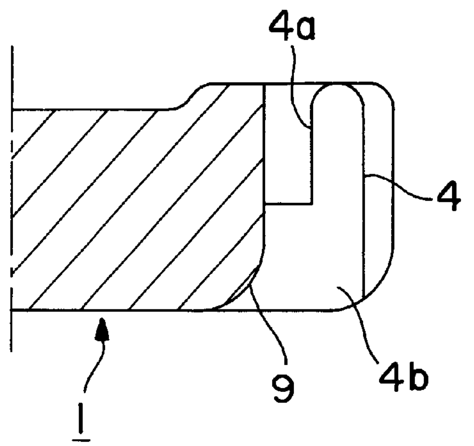
FIGS. 6(*a*) and 6(*b*) are illustrations showing another structural example of the first embodiment.
Figure 6B:
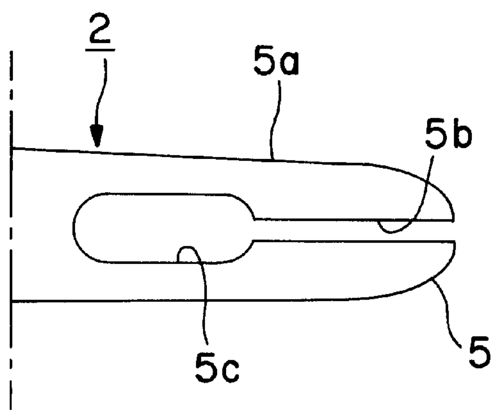

FIG. 6 is an illustration showing another structural example of this embodiment. Although with the needle stand 4, the guide passage 9 is formed from a midway portion of the needle stand recess 4*a*, the guide passage 9 can be in any form as far as no edge is formed to damage the suture 3B, and as shown in FIG. 6(*a*), the guide passage 9 can start from the bottom of the needle stand recess 4*a*.

Although in the needle receiver 5 of this embodiment, the slit 5*b* is formed in a liner groove shape, any slit may be used as far as a portion clamping the needle body 3A has a slightly narrower width than the diameter of the needle body, and as shown in FIG. 6(*b*), a piercing hole may be formed on a handle side of the lever 2 to adjust the needle retaining force of the needle receiver 5. The needle holder can enjoy substantially the same advantages by forming not a slit but a long hole.

Figure 7:
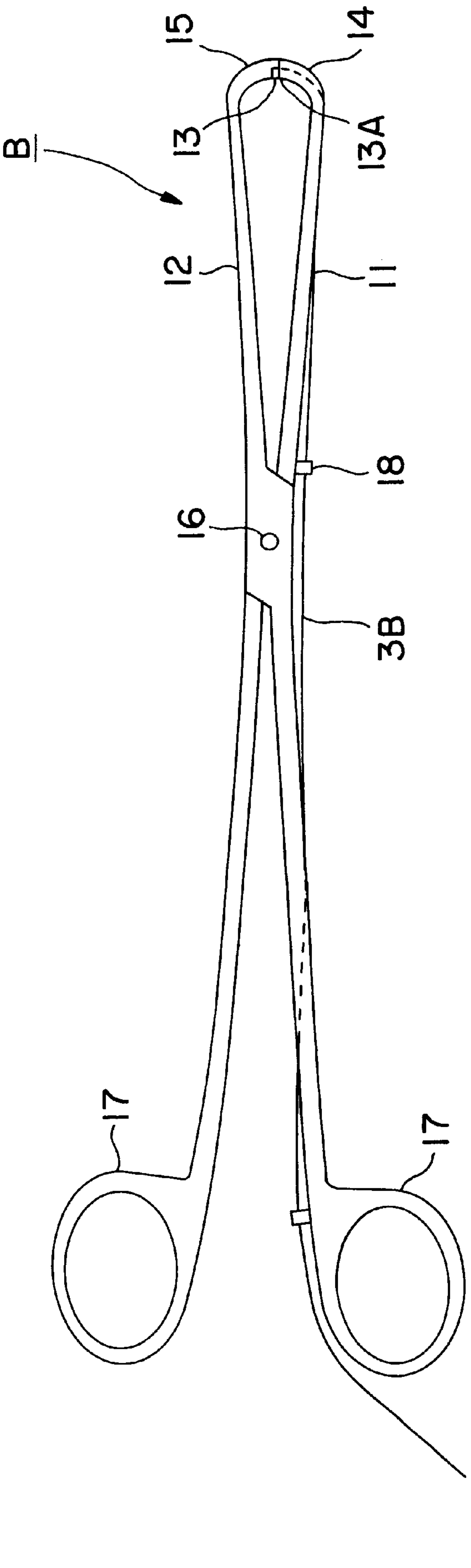
FIG. 7 is a side view showing a needle holder according to a second embodiment of the invention.
Figure 8:
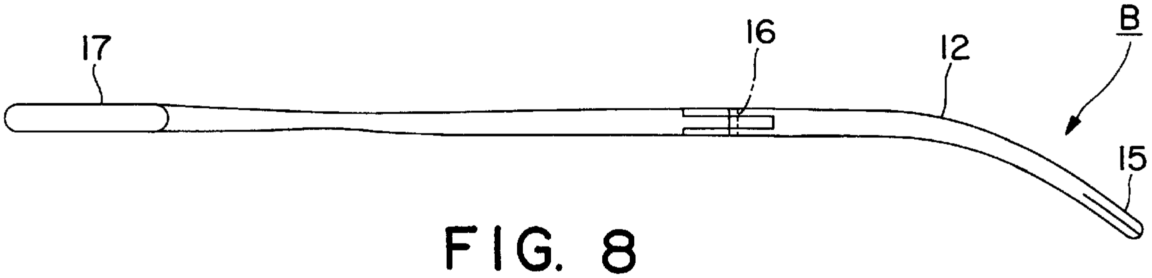
FIG. 8 is a plan view showing the needle holder of the second embodiment.
Figure 9:
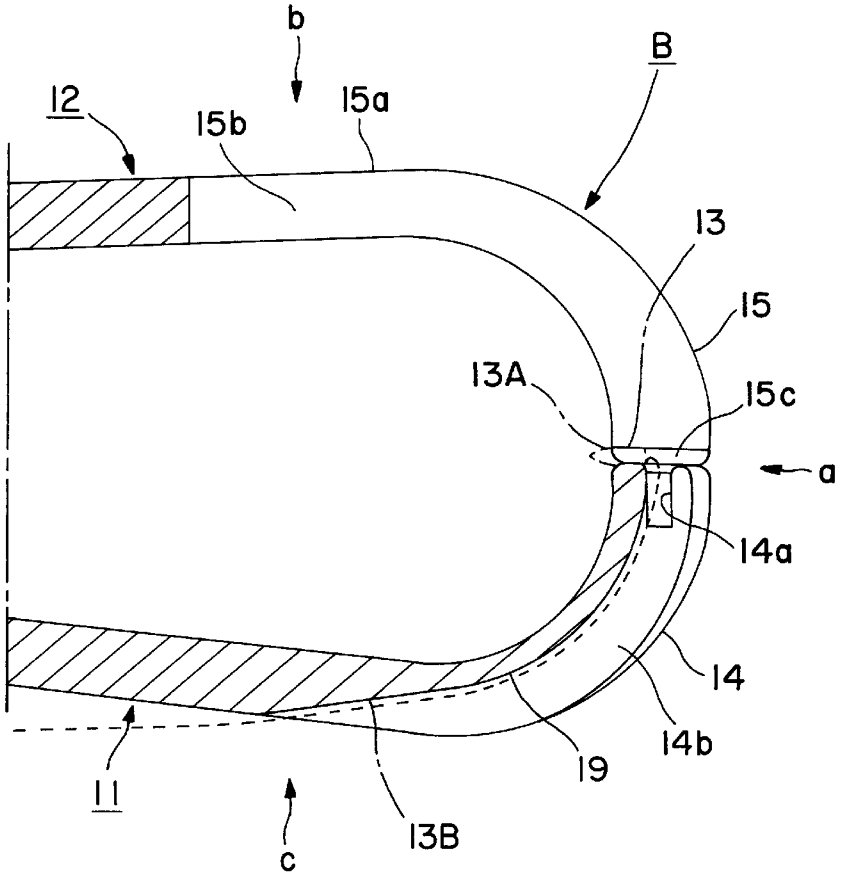
FIG. 9 is an enlarged side view showing a needle stand and a needle receiver of the needle holder of the second embodiment.
Figure 10A:
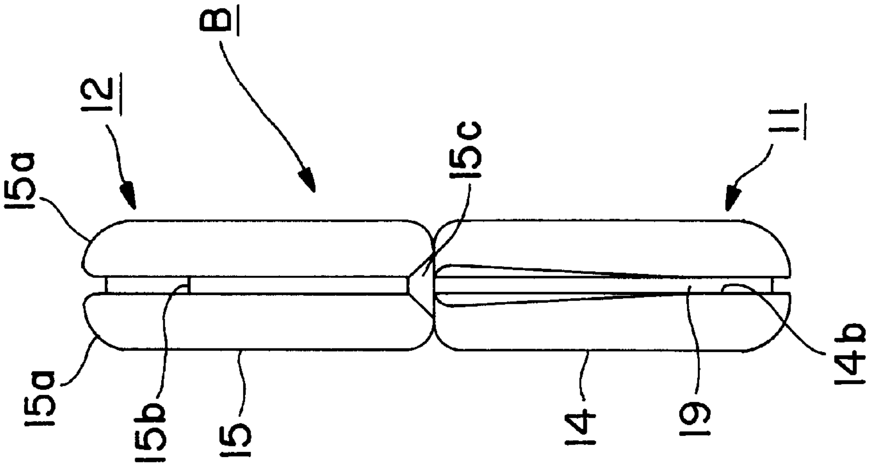
FIGS. 10(*a*) to 10(*c*) are views showing a distal end of the needle holder, in which FIG. 10(*a*) is a front view showing the distal end of the needle holder when seen in a direction of arrow a in FIG. 9, in which FIG. 10(*b*) is a plan view showing the distal end of the needle holder when seen in a direction of arrow b in FIG. 9, and in which FIG. 10(*c*) is a bottom view showing the distal end of the needle holder when seen in a direction of arrow c in FIG. 9.
Figure 10B:
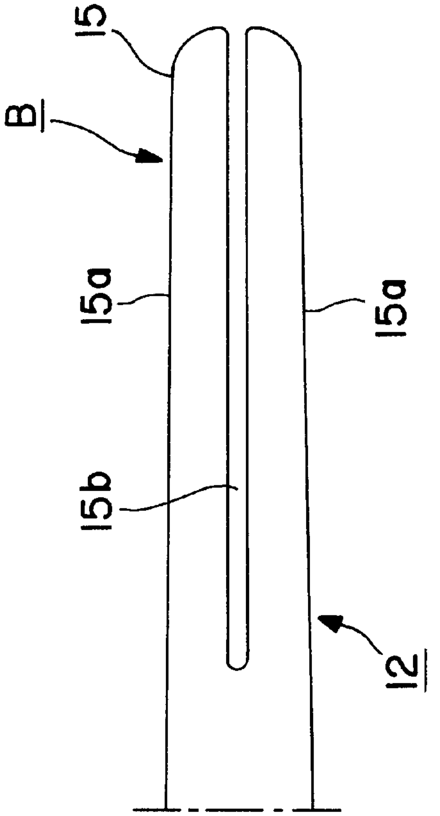
Figure 10C:
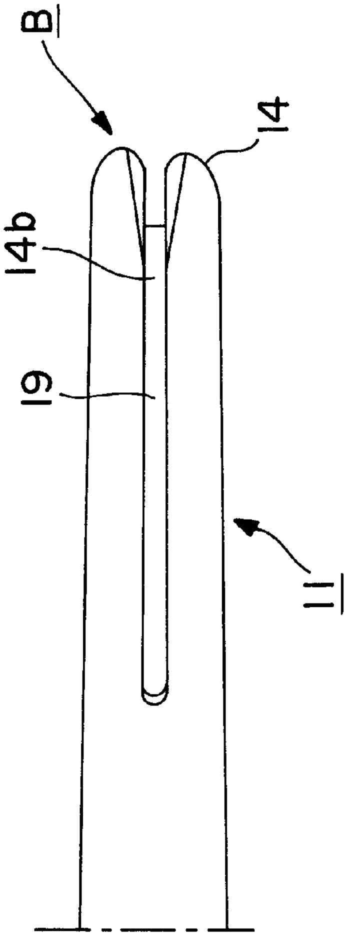

A second embodiment of the invention is described using FIGS. 7 to 10. FIG. 7 is a side view showing the whole shape of the needle holder of this embodiment; FIG. 8 is a plan view showing the needle holder; FIG. 9 is an enlarged view of a needle stand and a needle of the needle holder; FIGS. 10(*a*) to 10(*c*) are enlarged views of the needle stand and the needle receiver when seen in directions of arrows a,b,c, respectively, in FIG. 9.

The needle holder B shown in FIGS. 7, 8, is a forceps type guide instrument in which levers 11, 12 are crossed and connected pivotally around a pin 16 in substantially the same manner as the needle holder A. A needle stand 14 is formed on a distal end of the first lever 11, and a needle receiver 15 is formed on a distal end of the second lever 12. Handles 17 are formed on the opposite ends of the levers 11, 12, respectively.

Those levers 11, 12 are curved in a direction and has a shape capable of easily orienting the needle stand 14 and the needle receiver 15 to an area where operation is executed. Each of the needle stand 14 and the needle receiver 15 has an appearance largely curving in a letter C-shape, thereby enabling the needle stand 14 and the needle receiver 15 reach to a back side of large living tissues or astride another forceps to the back side of the forceps.

A needle 13 having a suture constituted of a needle body 13A and a suture 13B is placed on the needle stand 14 on the distal end of the lever 11. The suture 13B is guided to a side of the handle 17 from the needle stand 14 through plural suture guide members 8 formed at prescribed positions on the first lever 11.

Referring to FIGS. 9, 10, structures of the needle stand 14 and the needle receiver 15 are described. FIG. 9 is a side cross-sectional view in enlarging a tip portion of the needle holder B; FIGS. 10(*a*) to 10(*c*) are plan, front, and bottom views when seen in directions of arrows a,b,c, respectively, in FIG. 9.

The needle stand 14 is formed with a slit 14*b* and has a needle stand recess 14*a*. An opening of the needle stand recess 14*a* has no edge, in the same way as the above needle holder A, to avoid the suture 13B from suffering damages.

A guide passage 19 for suture 13B is formed along the slit 14*b* of the needle stand 14. The guide passage 19 is formed in a U-shaped groove opened outwardly from the top end to the bottom end.

The needle receiver 15 includes a slit 15*b* having a width smaller than the diameter of the needle body 13A and a prescribed length in the same way as the above needle holder A. Clamping arms 15*a*, 15*a* are formed on the opposite ends of the needle receiver 15. A needle retaining portion 15*c* is formed at a contact portion of the needle receiver 15 with the needle stand 14, and the needle retaining portion 15*c* can hold the needle with the suture as laid where the needle stand 14 and the needle receiver 15 are in contact with each other. The needle retaining portion 15*c* may have a narrower space or no space as closer to the distal end.

The needle holder B has curved levers 11, 12 as described above, and the surgeon can orient the needle stand 14 and the needle receiver 15 easily to living tissues to be ligated or sutured, so that the needle holder B is very easily handled depending on the area to be operated. The needle stand 14 and the needle receiver 15 curving in a the letter C-shape can do for suturing and ligating works by going behind living tissues larger than those for the needle holder A of the above embodiment, so that again the needle holder B is very easily handled depending on the area to be operated.

It is to be noted that the fundamental functions of the needle stand 14 and the needle receiver 15, as well as setting of the needle retaining portion 15*c* are substantially the same as those of the needle holder A of the first embodiment, and a duplicated description is omitted for the sake of simplicity.

Figure 11:
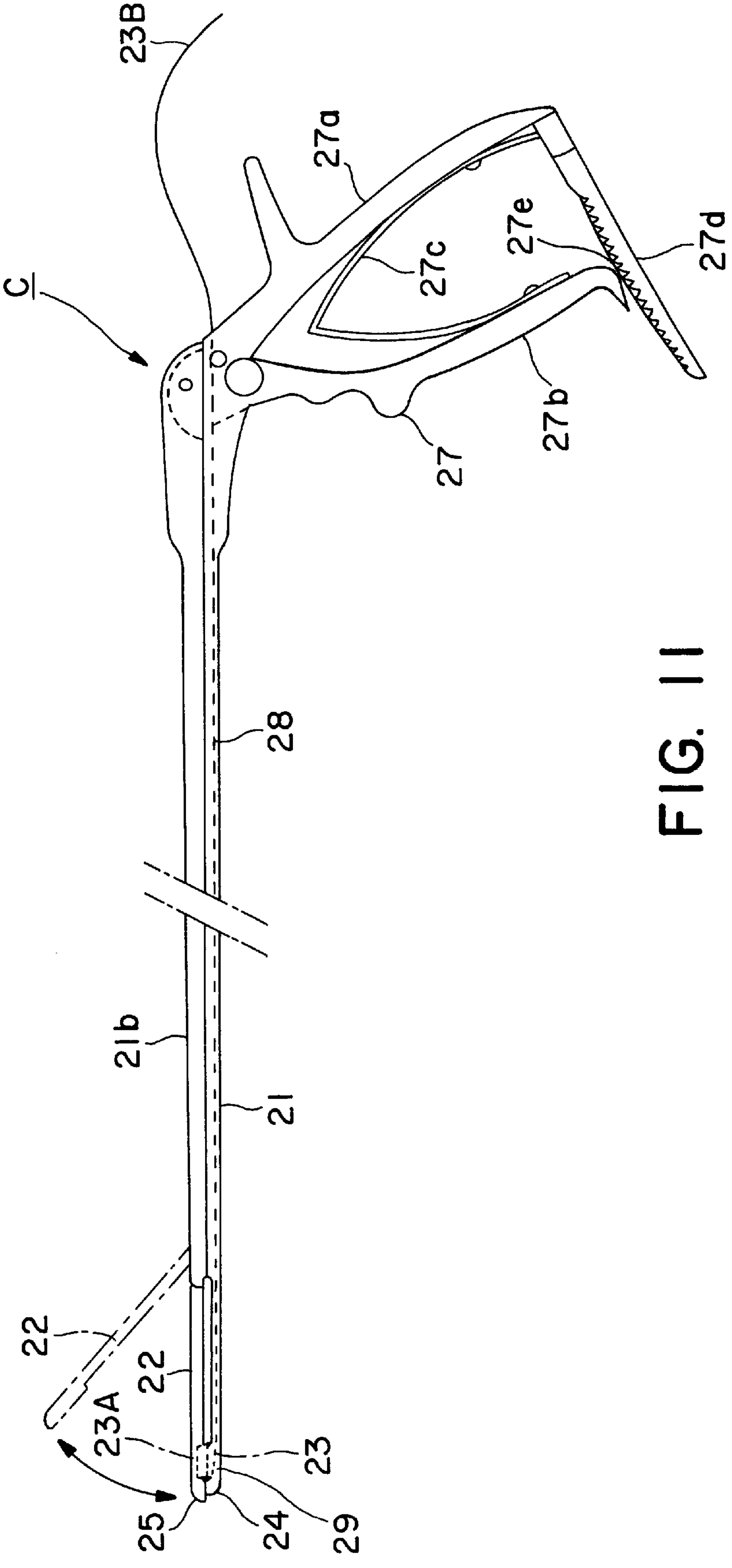
FIG. 11 is a side view showing a needle holder according to a third embodiment of the invention.

Referring to FIG. 11, a third embodiment of the invention is described. FIG. 11 shows a side view of a needle holder of a rod type. This rod type needle holder C is mainly used for an abdominal distension method in which a gas such as carbonate gas is supplied into an abdominal cavity to form a space within the abdominal cavity by the pressure of the gas for convenience of operation. With this method, a cylindrical trocar having an inner flange type valve is embed in the incised area of the abdomen, and the needle holder is introduced through the inside of the trocar into the abdominal cavity, thereby preventing the gas pressure in the abdominal cavity from leaking away.

The needle holder C of this embodiment is formed with a needle stand 24 on a distal end of a rod shape body 21 serving as a first shaft; a swinging arm 22 serving as a second shaft is pivotally connected around the distal end of the rod shape body 21 so as to be open and closed by a movable rod 21*b*; a needle receiver 25 is formed on a tip of the swinging arm 22.

A handle 27 is attached to the rear end of the rod shape body 22, and a trigger urged by a spring 27*c* is movably connected to a handle base 27*a* secured to the rod shape body 22. The trigger 27*b* and the swinging arm 22 are connected by the movable rod 21*b*, and the swinging arm 22 is pivotally moved by moving the trigger 27*b*, thereby rendering the needle receiver 25 closer to or separated from the needle stand 24.

The handle 27 has a rack bar 27, which can immobilize the opening and closing of the needle stand 24 and the needle receiver 25 by meshing a ratchet 27*e* formed on a tip of the trigger 27*b*.

A needle 23 having a suture placed on the needle stand 24 is constituted, in substantially the same way as the above two embodiments, of a needle body 23A and a suture 23B. The guide passage 29 is formed near the needle stand 24, and the suture 23B of the needle 23 having the suture is guided to the suture guide member 28 through the guide passage 29. The guide passage 29 is formed of a smooth long groove extending from the needle stand 24 to the suture guide member 28. No edge is formed in contact with the suture 23B when tension is given to the suture 23B.

Here, the structures of the needle stand 24 and the needle receiver 25 are not described in detail, but a needle retaining portion for retaining the needle body 23A as laid, a needle stand recess for rendering the needle body 23A upright, and clamping arms for clamping the needle body 23A, and so on have substantially the same structures as those of the needle holders A, B of the first, second embodiments. Setting of the needle receiver 25 is substantially the same as that of the needle holder A of the first embodiment, and a duplicated description is omitted for the sake of simplicity.

In the needle holder C according to this embodiment, although the guide passage 29 is structured of the long groove, the passage can be a pipe shape. The guide passages 9, 19 of the first and second embodiments can be made in a pipe shape to render the passages closed type.

Although in the needle holder C of this embodiment the upper shaft is made of the swinging arm, the lower shaft only or both of the upper and lower shafts can be a swinging arm or arms.

As described above, though use in a case of the endoscopic treatments is mainly described here, the needle holder according to the invention can be used for operation of living tissues in areas where a hand or other instrument cannot reach easily even for operation of opening an abdomen or a chest.

Although the using method that the needle is laid first is described in the above embodiment, the first work can be done by making the needle body upright without closing the levers completely and transferring the needle.

Although in the above embodiments, the lever is made of a stainless steel, the lever can be made of other materials. Particularly, the needle receivers 5, 15, 25 can be made of other materials such as resin, rubber, and so on. In such as a case, setting of the needle retaining force has the same limitations as those described above.

The foregoing description of preferred embodiments of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention should not be limited by the specification, but defined claims set forth below.

What is claimed is:

1. A needle holder for guiding a surgical needle having a suture attached to the needle, in which the surgical needle is transferred from a first shaft to a second shaft, comprising:

a first shaft;

a second shaft pivotally connected to said first shaft;

a needle stand comprising a recess slightly larger than a needle body to be used formed on the first shaft, within which the needle having the suture may be stood upright by applying tension upon the suture;

a needle receiver having a slit at a center thereof and a needle retaining portion formed on the second shaft which receives and retains the needle by clamping the needle at the slit through pivoting action of the first and second shafts; and a guide passage formed longitudinally on the first shaft with a bottom inclined in a curved shape and inclined towards the needle stand for guiding the suture attached to the needle from the needle stand in a prescribed direction to at least the vicinity of the needle stand, the guide passage having a surface that has no edge which may damage the suture regardless of the direction of the tension exerted upon the suture, wherein said needle retaining portion has a width smaller than a diameter of a needle body to be used to thereby exert a retaining force upon the needle.

2. A needle holder for guiding a surgical needle having a suture attached to the needle, in which the surgical needle is transferred from a first shaft to a second shaft, comprising:

a first shaft;

a second shaft pivotally connected to said first shaft;

a needle stand comprising a recess slightly larger than a needle body to be used formed on the first shaft, within which the needle having the suture may be stood upright by applying tension upon the suture; and a needle receiver having a needle retaining slit formed on the second shaft for receiving the needle made to stand upright at the needle stand through pivoting action of the first and second shafts to bring first and second shafts close to each other, said needle retaining slit having a width smaller than the diameter of the needle, which retains the needle by clamping of the needle, and a guide passage having smooth surfaces which do not damage the suture regardless of the direction of the tension applied thereon formed on the first shaft for guiding the suture attached to the needle from the needle stand in a prescribed direction to at least the vicinity of the needle stand, said needle receiver exerting a needle retaining force upon the needle according to the following formula I:

$$\phi * 1.5 \text{ kgf} \geqq \text{needle retaining force} \geqq 0.005 \text{ kqf} \quad \text{(I)}$$

wherein $\phi$ represents the diameter of the needle in millimeters.

3. The needle holder according to claim 2, wherein the guide passage is a groove extending in a longitudinal direction of the first shaft and having a bottom inclined in a curved shape.

4. The needle holder according to claim 2, wherein the needle receiver has a slit at a center of the needle receiver and receives the needle having the suture attached to the needle by clamping the needle at the slit.

* * * * *